(12) United States Patent
Chong et al.

(10) Patent No.: US 7,846,137 B2
(45) Date of Patent: Dec. 7, 2010

(54) MODULAR CATHETER SYSTEM

(75) Inventors: Colin Chong, Glendale, CA (US);
Rafael Bikovsky, Oak Park, CA (US);
Ronnie Paul Mounce, Burbank, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1486 days.

(21) Appl. No.: 10/746,308

(22) Filed: Dec. 26, 2003

(65) Prior Publication Data

US 2005/0148955 A1 Jul. 7, 2005

(51) Int. Cl.
*A61M 5/31* (2006.01)

(52) U.S. Cl. ...................................... 604/243

(58) Field of Classification Search ................. 604/534, 604/502, 103.09, 167.06, 243, 526, 891.1, 604/533, 284
See application file for complete search history.

(56) References Cited

U.S. PATENT DOCUMENTS

| | | | |
|---|---|---|---|
| 4,340,615 A | 7/1982 | Goodwin et al. | |
| 4,668,217 A | 5/1987 | Isono | |
| 4,969,879 A | 11/1990 | Lichte | |
| 5,000,190 A | 3/1991 | Petre | |
| 5,129,891 A | 7/1992 | Young | |
| 5,272,012 A | 12/1993 | Opolski | |
| 5,312,337 A | 5/1994 | Flaherty et al. | |
| 5,428,123 A | 6/1995 | Ward et al. | |
| 5,529,914 A | 6/1996 | Hubbell et al. | |
| 5,549,554 A * | 8/1996 | Miraki | 604/101.05 |
| 5,573,934 A | 11/1996 | Hubbell et al. | |
| 5,702,372 A | 12/1997 | Nelson | |
| 5,713,923 A * | 2/1998 | Ward et al. | 607/3 |
| 5,723,588 A | 3/1998 | Donofrio et al. | |
| 5,733,524 A | 3/1998 | Bucala et al. | |

(Continued)

FOREIGN PATENT DOCUMENTS

EP 0086338 8/1983

(Continued)

OTHER PUBLICATIONS

Program for Plasma Polymerization/Deposition Symposium, *Second International Symposium on Polymer Surface Modification: Relevance to Adhesion*, pp. 1-12.

(Continued)

*Primary Examiner*—Kevin C Sirmons
*Assistant Examiner*—Deanna K Hall
(74) *Attorney, Agent, or Firm*—Foley & Lardner LLP

(57) ABSTRACT

A modular catheter system. The modular catheter system may include a first tubular member, a first catheter tubing, a second tubular member, a second catheter tubing and a plurality of concentric seals. The first catheter tubing may be disposed within an interior portion of the first tubular member while the second catheter tubing may be disposed within an interior portion of the second tubular member. The first tubular member and the second tubular member are removably attachable to each other. The plurality of concentric seals may encircling the first catheter tubing and the second catheter tubing, and the first catheter tubing and the second catheter tubing form a continuous path when the first tubular member and the second tubular member are removably attached to each other. The catheter system may also be formed as a dual lumen catheter.

32 Claims, 12 Drawing Sheets

U.S. PATENT DOCUMENTS

| | | | |
|---|---|---|---|
| 5,833,275 | A | 11/1998 | Andersen |
| 5,874,277 | A | 2/1999 | Shintani et al. |
| 5,882,047 | A | 3/1999 | Ostrander et al. |
| 5,916,192 | A | 6/1999 | Nita et al. |
| 5,922,161 | A | 7/1999 | Wu et al. |
| 6,003,906 | A | 12/1999 | Fogarty et al. |
| 6,004,310 | A | 12/1999 | Bardsley et al. |
| 6,183,444 | B1 * | 2/2001 | Glines et al. ............... 604/187 |
| 6,210,378 | B1 | 4/2001 | Ouchi |
| 6,299,583 | B1 | 10/2001 | Eggers et al. |
| 6,358,238 | B1 | 3/2002 | Sherry |
| 6,663,606 | B1 | 12/2003 | Barry et al. |
| 6,666,839 | B2 * | 12/2003 | Utterberg et al. ........... 604/5.01 |
| 7,303,553 | B2 * | 12/2007 | Ott ............................. 604/533 |
| 2003/0004520 | A1 | 1/2003 | Haarala et al. |

FOREIGN PATENT DOCUMENTS

EP          0 343 910        11/1989

OTHER PUBLICATIONS

Brian Rudie, Osmonics, *Hydrophilicity and Hydrophobicity*, pp. 1-9.

Richard H. Griffey et al., Biophysical Journal/Biophysical Society, *Characterization of the Carbamino Adducts of Insulin*, vol. 54, Aug. 1988, pp. 295-300.

Ewa Ciszak et al., Current Biology Ltd ISSN 0969-2126, *Role of C-Terminal B-Chain Residues in Insulin Assembly: The Structure of Hexameric Lys$^{B28}$Pro$^{B29}$-human insulin*, Jun. 1995, vol. 3 No. 6, pp. 615-622.

Partial PCT International Search Report as issued in Internal U.S. Appl. No. PCT/US2004/041931, Mailing date May 3, 2005.

PCT International Search Report dated Aug. 9, 2005 for PCT/US2004/041931.

International Preliminary Report on Patentability and Written Opinion, dated Jun. 26, 2006, from related PCT/US2004/041931.

* cited by examiner

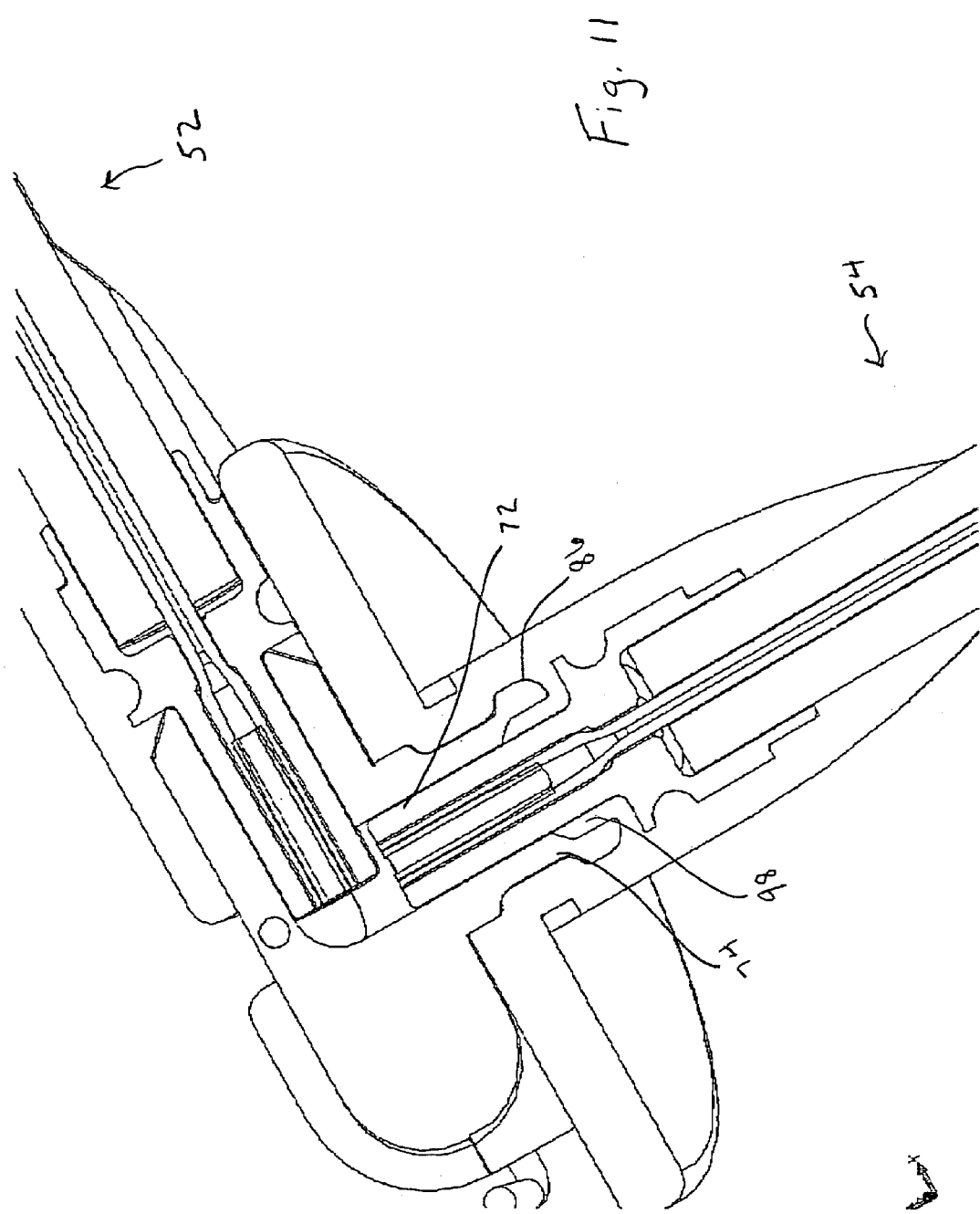

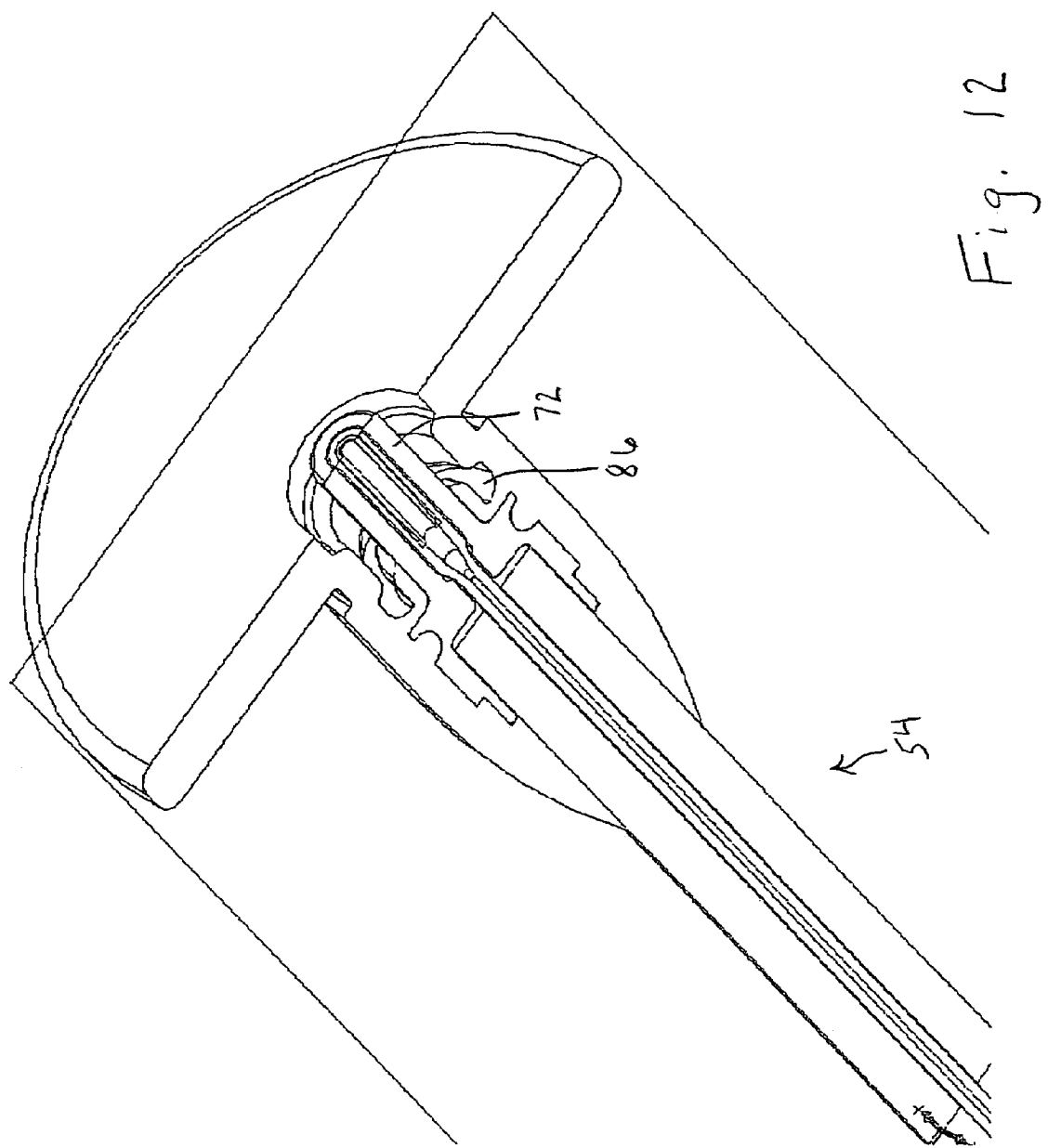

MODULAR CATHETER SYSTEM

BACKGROUND

1. Field of the Invention

Embodiments of the present invention relate to catheter technology and, in particular, to modular catheter systems having removable catheter portions.

2. Description of Related Art

The use of implantable devices to remedy medical conditions is becoming increasingly frequent as the size and cost of such devices shrinks and as the devices become easier to use. Many patients who, in the past, were forced to make routine visits to a medical professional for treatment or analysis or who were forced to self-administer treatment now rely on implanted devices to treat and analyze various medical conditions, thereby alleviating or eliminating the burden of trips to the hospital or doctor's office and the physical and emotional difficulty of rendering treatment to oneself. The use of implantable devices has given many patients the freedom they once new before the onset of their medical conditions, or perhaps the freedom they've never known for those who have dealt with medical conditions their entire lives.

For example, many people with diabetes now rely on implanted infusion pumps to deliver insulin. Implanted infusion pumps, along with associated sensing and control electronics, are capable of determining an amount of insulin required by a patient and can deliver a bolus or basal rate of insulin. Frequent manual testing of blood glucose levels has been replaced by glucose sensing technology included with the pump. Also, the routine injection of insulin by the patient using a needle has been replaced by the internal delivery of insulin by the pump based on the glucose levels determined by the sensor. Accordingly, diabetic patients who have taken advantage of implanted infusion pumps enjoy a lifestyle similar to that enjoyed by non-diabetics.

Most implanted devices include catheters for a variety of reasons. For example, implanted catheters may be used to deliver an infusant, such as a drug or other medicant, or may be used to provide a path for sensing technology or electronic signals. Currently, many catheters used in conjunction with implantable devices, such as an implantable infusion pump, for example, typically connect directly to the implantable device, as can be seen in the pump-catheter system 2 shown in FIG. 1. In FIG. 1, a catheter 8 is a right-angled catheter that makes a direct connection into an implantable infusion pump 4 at a connection point 6. When the catheter 8 needs to be replaced, the entire catheter 8 is removed at the connection point 6. Although connecting the catheter directly to the implantable device appears to be a logical, simple way to make a connection to the device, in practice, such a connection can actually be inefficient and even detrimental to a patient.

For example, if an implantable pump is placed into a patient, a pocket of tissue, i.e., a "pump pocket," forms around the pump and, consequently, the interface between the pump and the catheter as well. Generally, if the catheter includes a sensor, the catheter will need replacement more often than the pump needs to be replaced or needs to be serviced. To replace the catheter, then, requires that the pump pocket be opened, a procedure that is time consuming and undesirable. Once a pump pocket forms, opening it may be traumatic for the patient, time consuming for both patient and doctor, expensive and can increase the risk of infection. Also, opening a pump pocket requires a hospital stay for the procedure and for observation. Thus, although connecting a catheter directly to an implantable device appears reasonable, a connection of this type is actually fraught with ramifications that work toward the detriment of the patient and the patient's care providers.

In addition, many catheters made today that are suitable for implantation are labor intensive from a manufacturing standpoint and costly from a sterilization standpoint. For example, catheters that are used in complex applications can themselves be complex devices requiring sophisticated, expensive parts. Moreover, many of these parts are sensitive, such as the polyethylene tubing used in some catheters, and must be sterilized using a sensitive technique such as EtO sterilization, for example. In order for implantable devices to be considered a routine prescription for the remedying of debilitating medical conditions, the catheters used in conjunction with such devices must themselves be manufacturing friendly and must interface with the implantable devices in such a way catheter replacement is not a risky, expensive time consuming procedure.

SUMMARY

It is therefore an object of embodiments of the present invention to provide a catheter system that is suitable for implantation into a human body. It is a further object of embodiments of the present invention to provide a catheter system that is manufacturing friendly and can be produced inexpensively relative to currently manufactured catheters. It is yet a further object of embodiments of the present invention to provide a catheter system that can be sterilized using simple, inexpensive sterilization techniques. It is yet a further object of embodiments of the present invention to provide a modular catheter system and a catheter system having concentric seals that facilitates catheter replacement without having to access pump pockets.

According to embodiments of the present invention, a catheter system may include a first tubular member; a first catheter tubing, the first catheter tubing disposed within an interior portion of the first tubular member; a second tubular member, the second tubular member being removably attachable to the first tubular member; a second catheter tubing, the second catheter tubing disposed within an interior portion of the second tubular member; and a plurality of concentric seals encircling the first catheter tubing and the second catheter tubing. The first catheter tubing and the second catheter tubing may form a continuous path when the first tubular member may be removably attached to the second tubular member. At least one of the plurality of concentric seals may be formed when the second tubular member is removably attached to the first tubular member.

The first tubular member may form an angle with the second tubular member when the second tubular member is removably attached to the first tubular member. The angle formed between the first tubular member and the second tubular member may be substantially a right angle.

The catheter system may further include a third catheter tubing, the third catheter tubing disposed within an interior portion of the first tubular member and adjacent the first catheter tubing; and a fourth catheter tubing, the fourth catheter tubing disposed within an interior portion of the second tubular member and adjacent the second catheter tubing. The third catheter tubing and the fourth catheter tubing may form a path or a continuous path when the second tubular member is removably attached to the first tubular member. The first catheter tubing may be concentric with the third catheter tubing and the second catheter tubing may be concentric with the fourth catheter tubing. At least one of the plurality of concentric seals formed when the second tubular member is removably attached to the first tubular member encircles the third catheter tubing and the fourth catheter tubing.

The first tubular member may include an extrusion and the second tubular member may include a recess. The extrusion of the first tubular member may fit into the recess of the second tubular member via friction.

The first catheter tubing may be a fluoropolymer. At least one of the plurality of concentric seals may be titanium. At least one titanium concentric seal may abut and encircle the fluoropolymer first catheter tubing. The first tubular member and the second tubular member may be silicone. The silicone first tubular member and the silicone second tubular member may abut and encircle at least one titanium concentric seal.

The catheter system may further include an anchoring portion at a proximal end of the second tubular member. The proximal end of the first tubular member may abut the anchoring portion of the second tubular member when the first tubular member is removably attached to the second tubular member.

Also, the catheter system may further include a coupling disposed at a distal end of the first tubular member. The coupling may be attachable to an implantable device, and the second catheter tubing may extend out of the second tubular member. The catheter system may further include a sensor disposed within an interior portion of the second tubular member.

According to embodiments of the present invention, an implantable catheter may include a housing, the housing having a removably attachable interface; a first tubing, the first tubing disposed within an interior portion of the housing; and a plurality of concentric seals disposed within the housing and encircling the first tubing. At least one of the plurality of concentric seals may be formed when the removably attachable interface is engaged by a peripheral device.

The implantable catheter may further include a second tubing disposed within an interior portion of the housing and adjacent the first tubing. The first tubing and the second tubing may be concentric. The first tubing may be a fluoropolymer. The at least one of the plurality of concentric seals may be titanium. The at least one titanium concentric seal may abut and encircle the fluoropolymer first tubing. The housing may abut and encircle the at least one titanium concentric seal. The housing may be plastic or silicone.

A method of implementing a catheter includes providing a first outer housing; providing at least one first lumen tubing, the at least one first lumen tubing being disposed within an interior portion of the first outer housing; sealing the at least one first lumen tubing with a first seal; and sealing the at least one first lumen tubing with a second seal. The first seal and the second seal may be concentric and the first seal and the second seal may encircle the at least one first lumen tubing.

The method may further include providing a second housing and providing at least one second lumen tubing. The second housing may be removably attachable to the first housing and the at least one second lumen tubing may form a path or a continuous path with the at least one first lumen tubing when the second housing is removably attached to the first lumen housing. At least one of the first seal and the second seal may be formed when the second housing is removably attached to the first housing.

The method may further include providing at least one third lumen tubing adjacent the at least one first lumen tubing and providing at least one fourth lumen tubing adjacent the at least one second lumen tubing. The at least one third lumen tubing may be concentric with the at least one first lumen tubing and the at least one fourth lumen tubing may be concentric with the at least one second lumen tubing.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 11 shows a cutaway view of a compression-fit interface between a first tubular member and a second tubular member of a modular catheter system according to an embodiment of the present invention.

FIG. 12 shows a perspective, cutaway view of compression-fit interface between a first tubular member and a second tubular member of a modular catheter system according to an embodiment of the present invention.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

The following description is directed primarily toward modular catheter systems and catheters having concentric seals; however, embodiments of the present invention may be implemented in a variety of ways and may be used in a variety of capacities and applications. For example, embodiments of the present invention may be used for implantable infusion pumps. Also, embodiments of the present invention may be used in vivo or may be used percutaneously. Generally, embodiments of the present invention may be adapted for use in any environment in which catheter replacement without having to access a pump pocket is desired or isolation of a catheter from its external environment is required.

Figure 1:
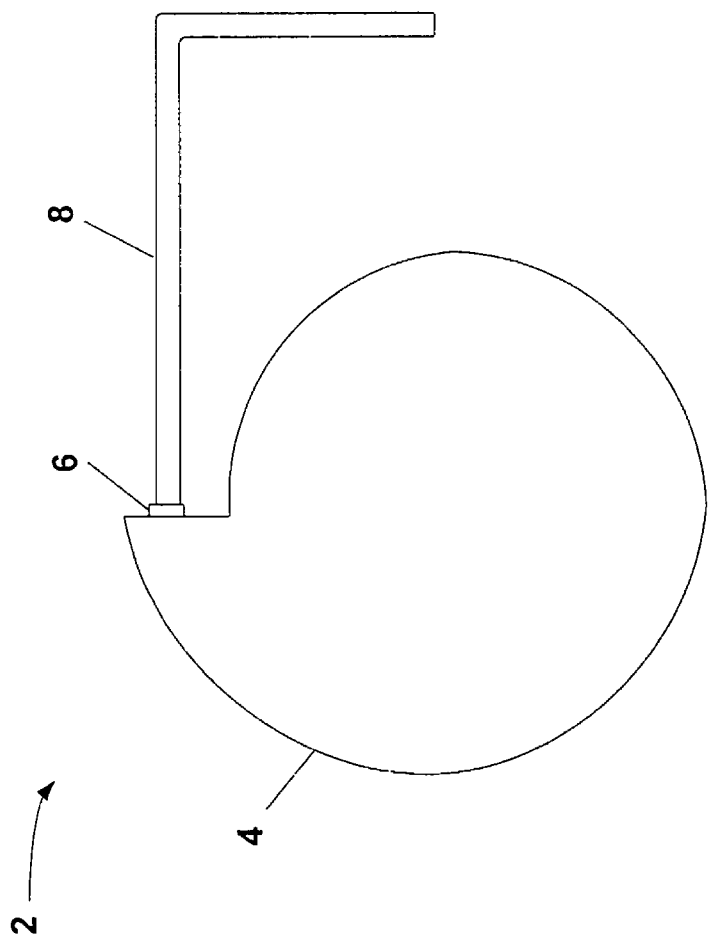
FIG. 1 shows a side view of a catheter system according to the prior art.
Figure 2:
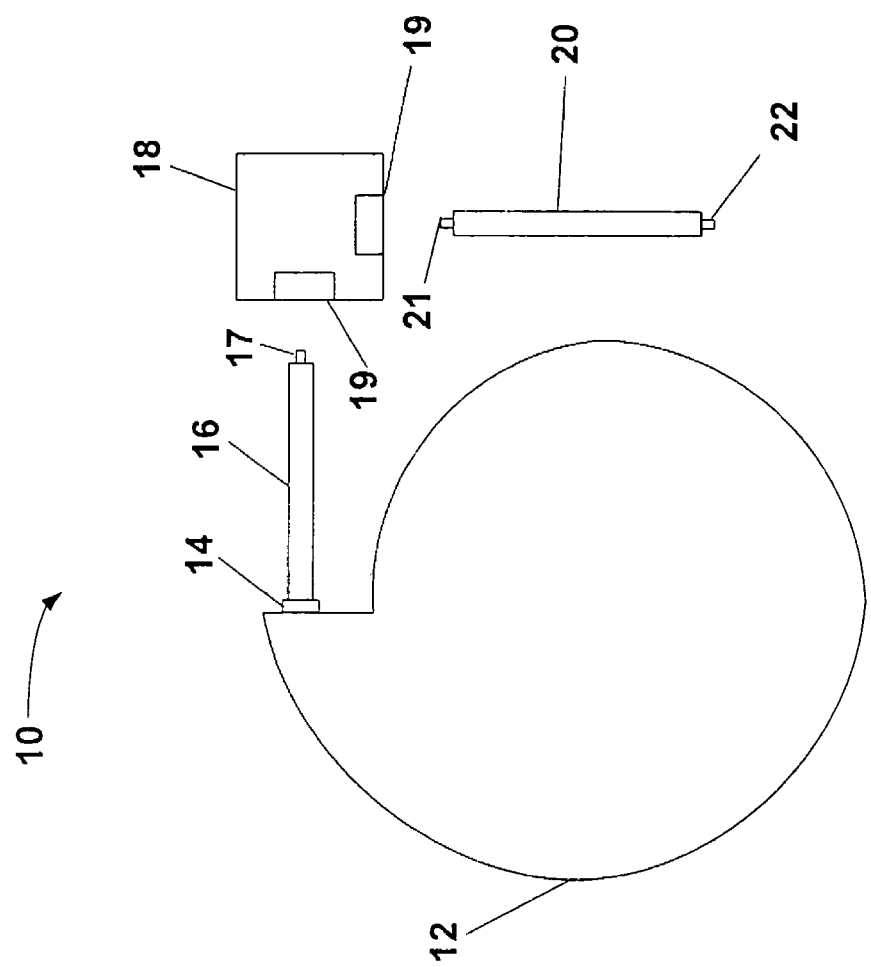
FIG. 2 shows a generalized block diagram of a modular catheter system according to an embodiment of the present invention.

FIG. 2 shows a generalized block diagram of a modular catheter system 10 according to an embodiment of the present invention. In the embodiment of the invention shown in FIG. 2, individual components of the modular catheter system 10 are modularized for ease of manufacturing and ease of replacement. The modular catheter system 10 shown in FIG. 2 includes, but is not limited to, a first tubular member 16, a junction 18 and a second tubular member 20. The individual components may be formed as a plurality of male-female pairs. For example, the modular catheter system 10 may be used in conjunction with an implantable device such as an implantable infusion pump 12. The implantable infusion pump 12 shown in FIG. 2 includes a female connection point 14. Accordingly, the first tubular member 16 may be formed to have two male catheter tubing ends, a first catheter tubing end of which interfaces with and connects to the female connection point 14, as shown. The second catheter tubing end 17 of the first tubular member 16 may interface with the junction 18.

Likewise, the second tubular member 20 may include a first male catheter tubing end 21 and a second male catheter tubing end 22. The junction 18 includes, but is not limited to, female connection points 19 into which the second catheter tubing end 17 of the first tubular member 16 and the first catheter tubing end 21 of the second tubular member 20 may be inserted. The second catheter tubing end 22 of the second tubular member 20 may be left unattached, thereby allowing a fluid such as insulin or other drug or medicant to be dispersed into its surround area.

Although the embodiment of the invention shown in FIG. 2 shows the first tubular member 16 and the second tubular member 20 having male ends and the junction 18 having female ports, a variety of male-female combinations may be used. For example, the first tubular member 16 and the second tubular member 20 may have female ports and the junction 18 may have male connectors. Also, the junction 18 may be independent of the first tubular member 16 and the second tubular member 20 or may be integrated into the first tubular member 16 and the second tubular member 20.

By manufacturing the modular catheter system 10 as shown in the embodiment of the invention in FIG. 2, the modular catheter system 10 may be made relatively inexpensively and with high reliability. The modularization of components results in high volume production while reducing costs. In addition, the manufacturing repeatability associated with modularization reduces product defects and increases reliability.

Also, the modular catheter system 10 facilitates catheter replacement after the modular catheter system 10 has been implanted into a patient. For example, in the embodiment of the invention shown in FIG. 2, two joints forming a right angle exist at the interface between the first tubular member 16 and the junction 18 and the second tubular member 20 and the junction 18. Because of the modularity of the modular catheter system 10, the first tubular member or the second tubular member may be removed at a joint, i.e., at the interface between one of the tubular members and the junction 18, without removing the other tubular member. Accordingly, tubular member replacement is facilitated. Thus, if, for example, the second tubular member 20 needs replacement, it may be removed from the junction 18 while the remainder of the modular catheter system 10 remains intact and in place. If a pump or other device to which the modular catheter system 10 is attached is surrounded by a pocket of tissue, the tissue need not be disturbed in order to replace a component of the modular catheter system 10.

Figure 3:
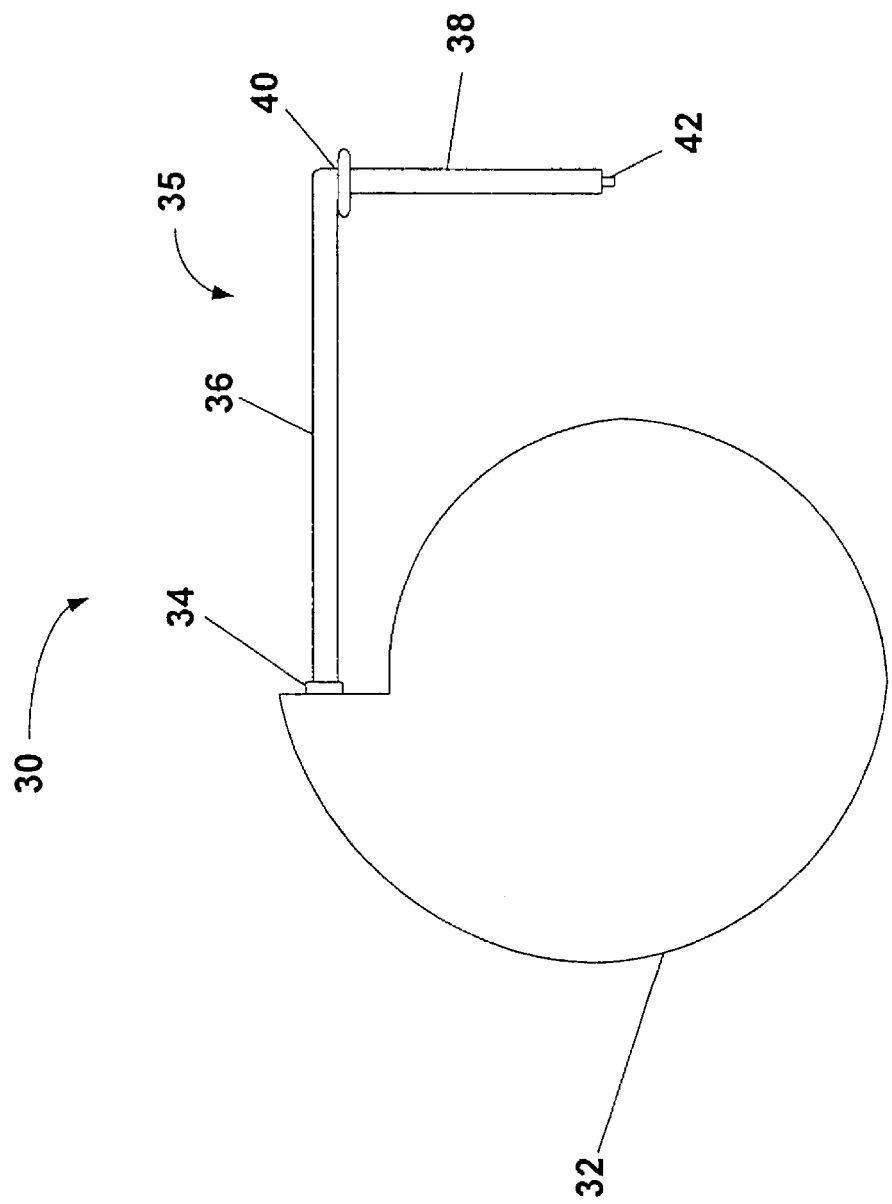
FIG. 3 shows an implantable system using a modular catheter system according to an embodiment of the invention.

FIG. 3 shows an implantable system 30 using a modular catheter system 35 according to an embodiment of the invention. In the embodiment of the invention shown in FIG. 3, the modular catheter system 35 includes, but is not limited to, a first tubular member 36 and a second tubular member 38. The first tubular member 36 interfaces and connects to an implantable device 32 at a connection point 34. The second tubular member 38 may include other elements, such as a sensor, for example. The first tubular member 36 and the second tubular member 38 may be removably attached to each other at a junction 40. A catheter tubing 42 extends out of the second tubular member 38 such that fluids may be released into the body. In addition, a sensor and associated components may be located within the catheter tubing 42.

The entire implantable system 30 may be implanted in a human body. According to one embodiment of the invention, after implantation, a pocket of tissue may form over the implantable device 32, the connection point 34 and a portion of the first tubular member 36. Over time, such as every one to two years, for example, a sensor disposed within the second tubular member 38 may need to be replaced or re-calibrated, thus requiring removal from the implantation point. In addition, over time, the tip of the catheter tubing 32 may become obstructed due to particulate build-up or other obstructions. When it becomes necessary to replace the sensor or the tip of the catheter tubing, the second tubular member 38 may be removed from the first tubular member 36. The first tubular member 36 need not be removed from the connection point 34.

According to the embodiment of the invention shown in FIG. 3, the pocket of tissue formed over the implantable device 32, the connection point 34 and a portion of the first tubular member 36 need not be opened. Because the modular catheter system 35 has been designed and fabricated in a modular fashion and because the first tubular member 36 may be removably attached to the second tubular member 38, the pocket of tissue may remain intact, thereby reducing the risk of infection. Moreover, the second tubular member 38 may be easily replaced with another unit in a minimally invasive fashion, thereby reducing the amount and severity of trauma to the patient.

Figure 4:
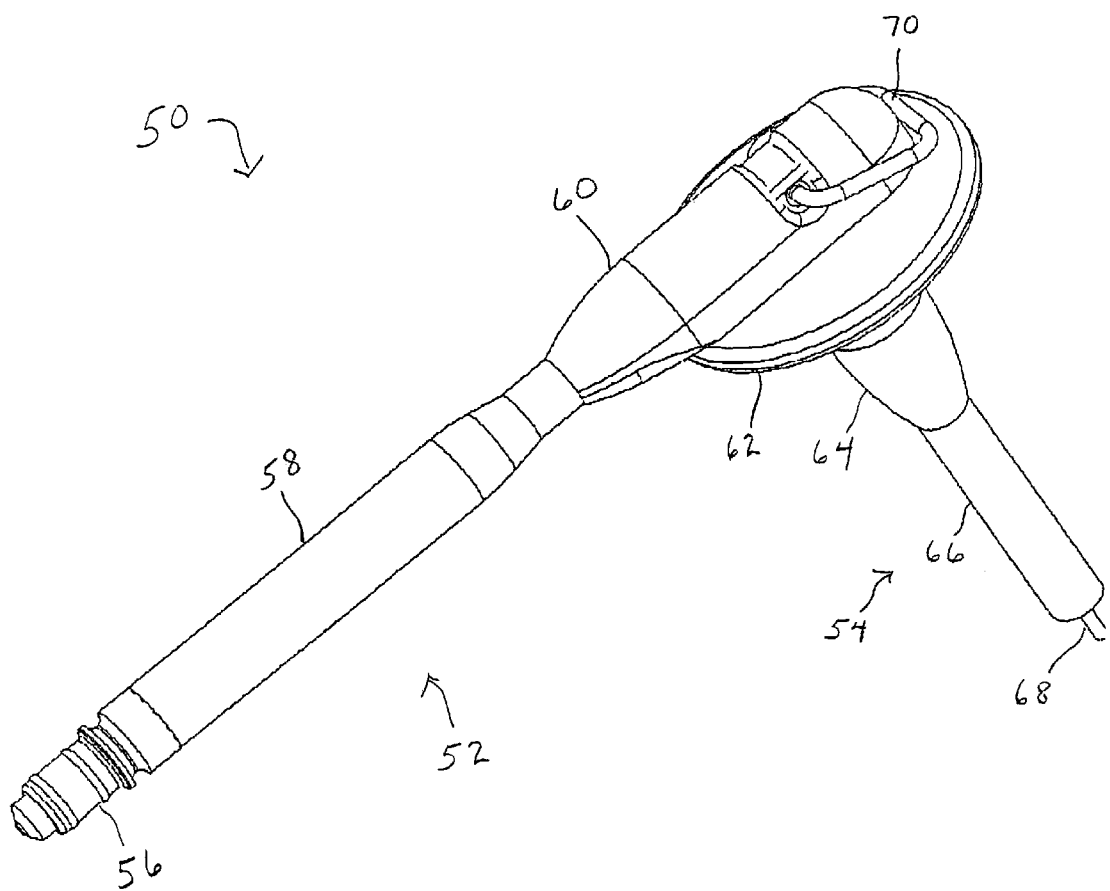
FIG. 4 shows a modular catheter system according to an embodiment of the present invention.

FIG. 4 shows a modular catheter system 50 according to an embodiment of the present invention. The modular catheter system 50 includes, but is not limited to, a first tubular member 52 and a second tubular member 54. In the embodiment of the invention shown in FIG. 4, the first tubular member 52 and the second tubular member 54 are removably attachable to each other. Thus, the modular catheter system 50 may be configured as a multi-member device. In the embodiment of the invention shown in FIG. 4, the modular catheter system 50 is configured as a two-member device. However, embodiments of the invention are not limited to two parts, and may be configured from three or more members. In addition, in the embodiment of the invention shown in FIG. 4, an angle which is substantially a right angle is formed when the first tubular member 52 and the second tubular member 54 are removably attached to one another.

The first tubular member 52 includes, but is not limited to, a coupling 56, a first outer housing 58 and a first header portion 60. Also included with the first tubular member 52 is a loop assembly 70 which may be used to hold or grip the modular catheter system 50 or the first tubular member 52 if necessary.

The second tubular member 54 includes, but is not limited to, a disc 62, a second header portion 64, a second outer housing 66 and a second catheter tubing 68. The first tubular member 52 and the second tubular member 54 may be made from bio-compatible, bio-stable materials. For example, the coupling 56, first outer housing 58, first header portion 60 and loop assembly 70 of the first tubular member 52 and the disc 62, second header portion 64, and second outer housing 66 of the second tubular member 54 may be made from silicone rubber or polyethylene.

The coupling 56 at a distal end of the first tubular member 52 may be designed to interface with an implantable device. For example, if the modular catheter system 50 shown in the embodiment of FIG. 4 were designed for use with an implantable infusion pump used to deliver insulin to diabetics, the coupling 56 could connect to a port on the implantable infusion pump.

The second catheter tubing 68 at a distal end of the second tubular member 54 may be located at a desirable position within the body of a patient, such as a patient's abdomen, for example. Insulin maintained within the implantable infusion pump may exit the pump and travel through the first tubular member 52 and the second tubular member 54, exiting through the second catheter tubing 68 into the patient.

The disc 62 at a proximal end of the second tubular member 54 may be formed to provided an anchor point for the first header portion 60 of the first tubular member 52. In addition, the disc 62 provides a point of leverage for a medical professional when removing the second tubular member 54 from the first tubular member 52, as will be explained in more detail below.

Figure 5:
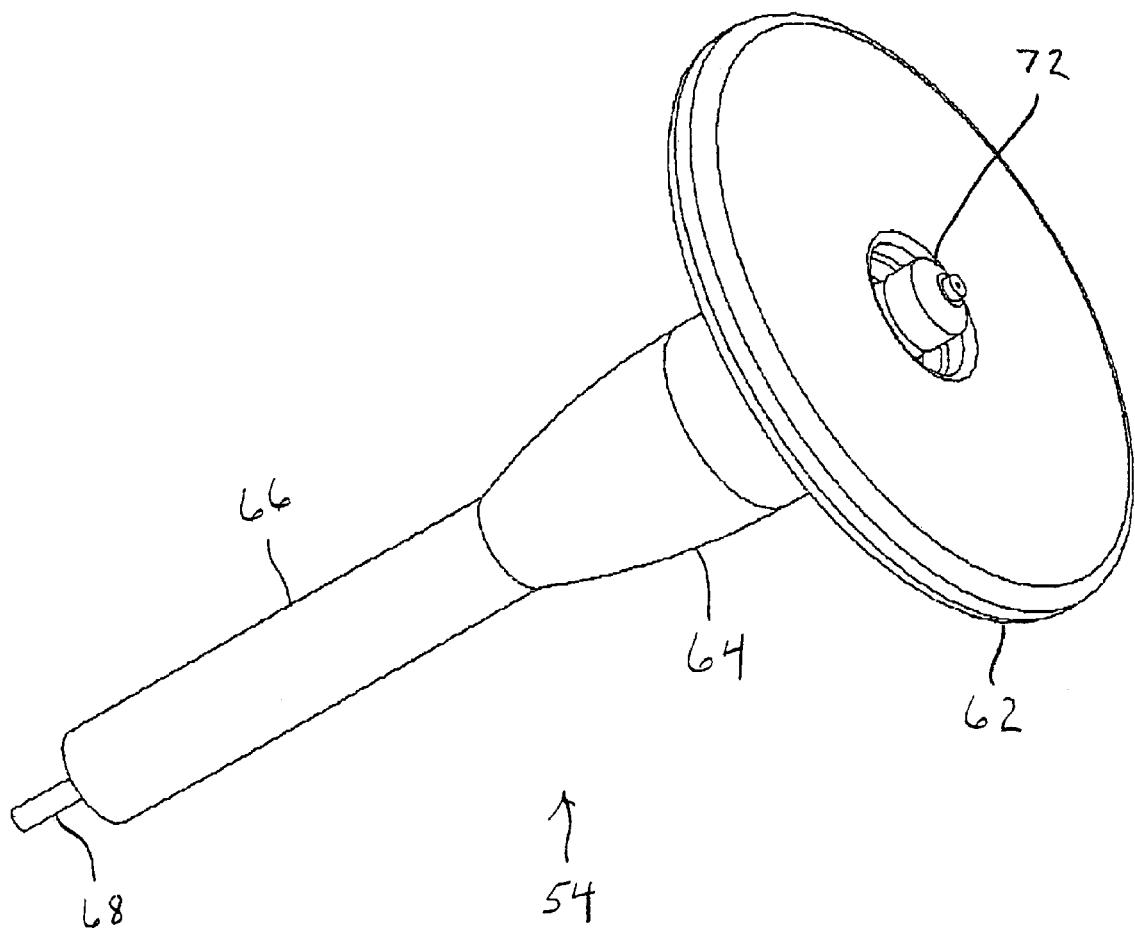
FIG. 5 shows a perspective, isolated view of a member of a modular catheter system according to an embodiment of the present invention.

FIG. 5 shows a perspective, isolated view of the second tubular member 54 according to an embodiment of the present invention. In addition to the disc 62, the second header portion 64, the second outer housing 66 and the second catheter tubing 68, FIG. 5 also shows a second seal molding 72. The second seal molding 72 engages and forms a connection with the first tubular member 52 as will be explained in greater detail below.

Figure 6:
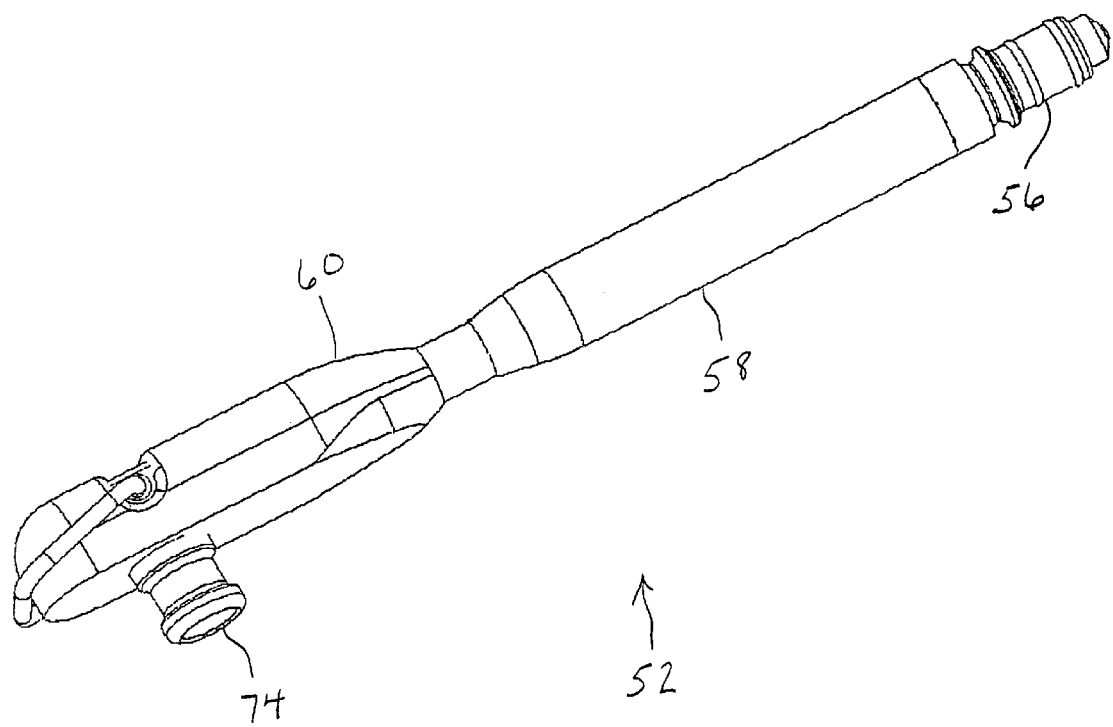
FIG. 6 shows a perspective, isolated view of a member of a modular catheter system according to an embodiment of the present invention.

FIG. 6 shows a perspective, isolated view of the first tubular member 52 according to an embodiment of the present invention. In addition to the coupling 56, the first outer housing 58 and the first header portion 60, FIG. 6 shows an extrusion 74. The extrusion 74 of the first tubular member 52 interfaces and forms a connection with the second seal molding 72 of the second tubular member 54, as will be explained in greater detail below.

Figure 7:
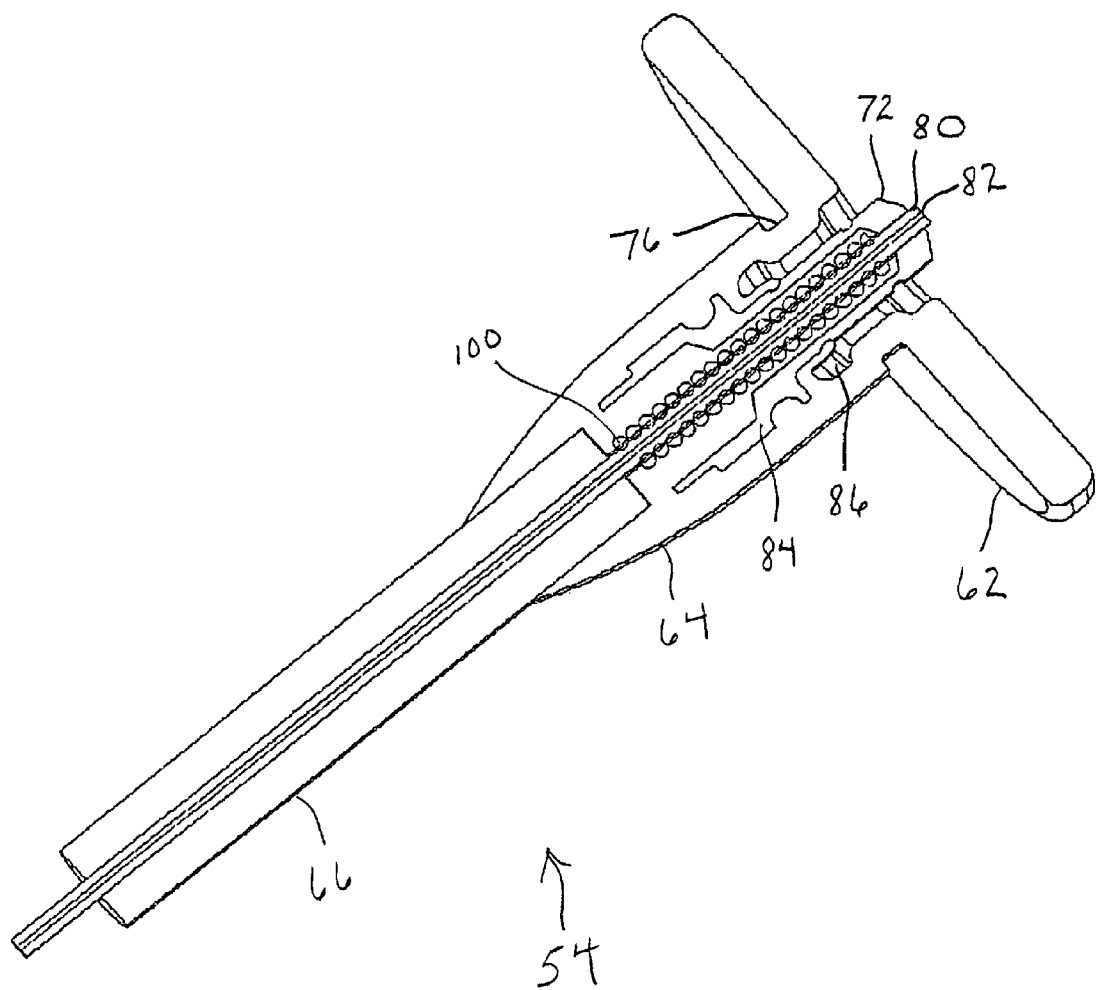
FIG. 7 shows a cutaway perspective view of a member of a modular catheter system according to an embodiment of the present invention.

FIG. 7 shows a cutaway perspective view of the second tubular member 54. According to the embodiment of the invention shown in FIG. 7, the second catheter tubing 68 includes, but is not limited to, a second outer lumen 80 and a second inner lumen 82. The second outer lumen 80 and the second inner lumen 82 extend the entire length of the second tubular member 54 and terminate at the end of the extrusion 74. In the embodiment of the invention shown in FIG. 7, the second outer lumen 80 and the second inner lumen 82 are concentric. A dual lumen catheter of the type shown in FIG. 7 is disclosed in U.S. patent application Ser. No. 10/036,081, filed Dec. 28, 2002, the contents of which are hereby incorporated by reference herein. However, the second catheter tubing 68 is not limited to the dual, concentric second outer lumen 80 and second inner lumen 82 shown in the embodiment of the invention in FIG. 7. The second catheter tubing 68 may comprise a single lumen or may comprise two or more lumens. Moreover, if the second catheter tubing 68 comprises two or more lumens, the lumens may be concentric or may be positioned otherwise adjacent to each other. For example, if the second catheter tubing 68 comprises two lumens, the lumens may be positioned side-by-side or have some other configuration advantageous to the application for which the catheter is being used.

Also shown in the embodiment of the invention in FIG. 7 is a first seal molding 84 and a second seal recess 86. The first seal molding 84 may be formed around the second catheter tubing 68 during manufacturing and may completely encircle the second catheter tubing 68. Thus, the first seal molding 84 may provide a first seal for the second catheter tubing 68. The first seal molding 84 may be made from a variety of bio-compatible, bio-stable, implantable grade materials. For example, according to an embodiment of the present invention, the first seal molding 84 may be made from titanium, stainless steel, any of a variety of plastics, any long term implantable material, and the like.

The second seal recess 86 provides an insertion area for the extrusion 74 of the first tubular member 52. The interface between the second seal recess 86 and the extrusion 74 of the first tubular member 52 will be described in greater detail below.

The second seal molding 72 may be made from a variety of bio-compatible, bio-stable, implantable grade materials. For example, according to an embodiment of the present invention, the second seal molding 72 may be made from TEFLON or other fluoropolymers, other long term implantable materials, and the like. A ring 76 for providing an additional seal may also be seen in FIG. 7. A first tubing coil 100, described in greater detail below, may also be seen in FIG. 7.

Figure 8:
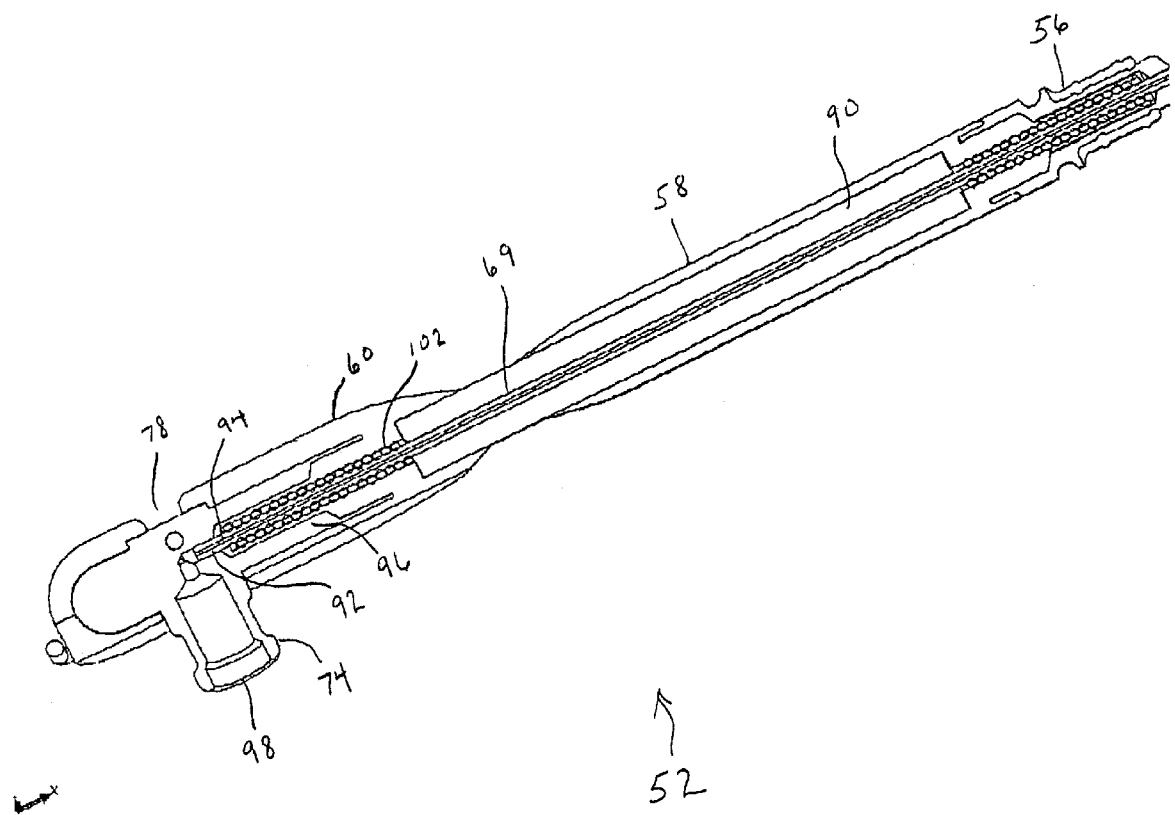
FIG. 8 shows a cutaway side view of a member of a modular catheter system according to an embodiment of the present invention.

FIG. 8 shows a cutaway side view of the first tubular member 52. In addition to the coupling 56, the first outer housing 58, the first header portion 60, the extrusion 74 and the loop assembly recess 78, FIG. 8 also shows a first inner housing 90, a first catheter tubing 69, an inner molding 96 and an extension recess 98. The first catheter tubing 69 includes, but is not limited to, a first outer lumen 92 and a first inner lumen 94.

The first catheter tubing 69 may extend the entire length of the first tubular member 52 and may terminate at an interior portion of the coupling 56. In the embodiment of the invention shown in FIG. 8, the first outer lumen 92 and the first inner lumen 94 of the first catheter tubing 69 are concentric, as was the case with the second outer lumen 80 and the second inner lumen 82 shown in FIG. 7. Also, and as was the case with the second outer lumen 80 and the second inner lumen 82 shown in FIG. 7, the first outer lumen 92 and the first inner lumen 94 need not be concentric, and may positioned otherwise adjacent to each other.

When the first tubular member 52 and the second tubular member 54 are removably attached to one another, the first catheter tubing 69 may form a path, which may be a continuous path, with the second catheter tubing 68. Thus, a fluid may pass through the entire length of the first tubular member 52 and the second tubular member 54 via the first catheter tubing 69 and the second catheter tubing 68. In addition, the path formed by the first catheter tubing 69 and the second catheter tubing 68 may be used for elements other than fluids. For example, for some applications, a sensor and sensor wires may be positioned within the first inner lumen 94 and the second inner lumen 82.

In the embodiment of the invention shown in FIG. 8, the first inner housing 90 may surround and seal the first catheter tubing 69. In addition, the inner molding 96 may be formed around the first catheter tubing 69 during manufacturing and may completely encircle the first catheter tubing 69. Thus, the inner molding 96 may provide a first seal for the first catheter tubing 69. The inner molding 96 may be made from a variety of bio-compatible, bio-stable, implantable grade materials. For example, according to an embodiment of the present invention, the inner molding 96 may be made from titanium, stainless steel, any of a variety of plastics, any long term implantable material, and the like.

According to an embodiment of the present invention, the extension recess 98 may provide an insertion area for the second seal molding 72 of the second tubular member 54. The interface between the extension recess 98 and the second seal molding 72 of the second tubular member 54 will be described in greater detail below.

Figure 9:
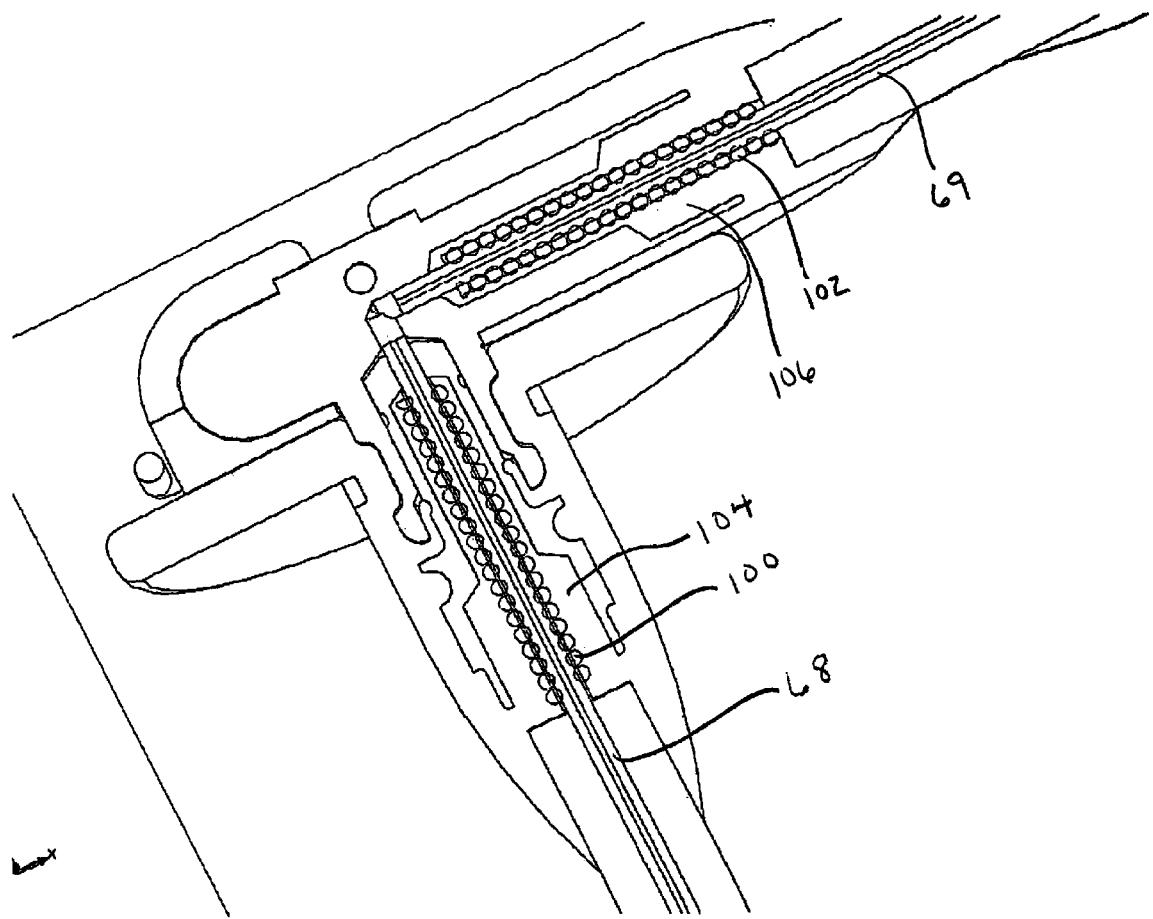
FIG. 9 shows a cutaway view of an anchoring mechanism for a modular catheter system according to an embodiment of the present invention

FIG. 9 shows anchoring mechanisms for the first catheter tubing 69 and the second catheter tubing 68 according to an embodiment of the present invention. In FIG. 9, a first tubing coil 100 and a second tubing coil 102 may surround a portion of the outer diameters of the first catheter tubing 69 and the second catheter tubing 68, respectively. The first and second tubing coils 100 and 102 may engage the outer diameters of the first catheter tubing 69 and the second catheter tubing 68, respectively, to maintain the position of each catheter tubing within respect to the tubing coils.

According to an embodiment of the present invention, the first and second tubing coils 100 and 102 may be frictionally connected to the first catheter tubing 69 and the second catheter tubing 68. Thus, in the embodiment of the invention shown in FIG. 9, a "tubing-to-tubing" connection may be made without internal support mechanisms, such as a clamp, for example.

If the first and second tubing coils 100 and 102 are twisted such that an inner diameter of each tubing coil increases, a catheter tubing may be inserted into each tubing coil 100 and 102. However, if the inner diameters of the tubing coils 100 and 102 are sized slightly smaller than the outer diameter of the first catheter tubing 69 and the second catheter tubing 68, such as a few thousandths of an inch, for example, the inner diameters of the first and second tubing coils 100 and 102 may grip the outer diameters of the first catheter tubing 69 and the second catheter tubing 68, respectively, when the first and second tubing coils 100 and 102 are released and not twisted. Thus, the "anchor points" for the first and second tubing coils 100 and 102 are transverse across the length of the first catheter tubing 69 and the second catheter tubing 68, respectively, rather than around the diameters of each tubing. Moreover, the load is distributed through each ring of the tubing coils.

If the first molding 104 and the second molding 106 are threaded with the same pitch as the tubing coils 100 and 102, the first catheter tubing 69 and the second catheter tubing 68 may be rotatably inserted into the moldings for placement. According to embodiments of the present invention, the tubing coils 100 and 102 may be glued into place. Also, the first and second tubing coils 100 and 102 may be designed such that the force exerted by the first and second tubing coils 100 and 102 on the first catheter tubing 69 and the second catheter tubing 68, respectively, is great enough to maintain the position of the first catheter tubing 69 and the second catheter tubing 68 with respect to the first and second tubing coils 100 and 102 but not so great that the inner diameters of the first catheter tubing 69 and the second catheter tubing 68 are deformed or altered in any way.

The first and second tubing coils 100 and 102 may be fabricated in a variety of ways. For example, according to embodiments of the present invention, the first and second tubing coils 100 and 102 may be springs. According to other embodiments of the present invention, the first and second tubing coils 100 and 102 may be threads, rings with clips, square springs, round springs, splines, wires wrapped as coils and the like. Also, the first and second tubing coils 100 and 102 may be designed as a "Chinese" tube, where the inner diameter of the coil decreases as the tube is "stretched." The first and second tubing coils 100 and 102 may be made from stainless steel, alloys and the like.

Figure 10:
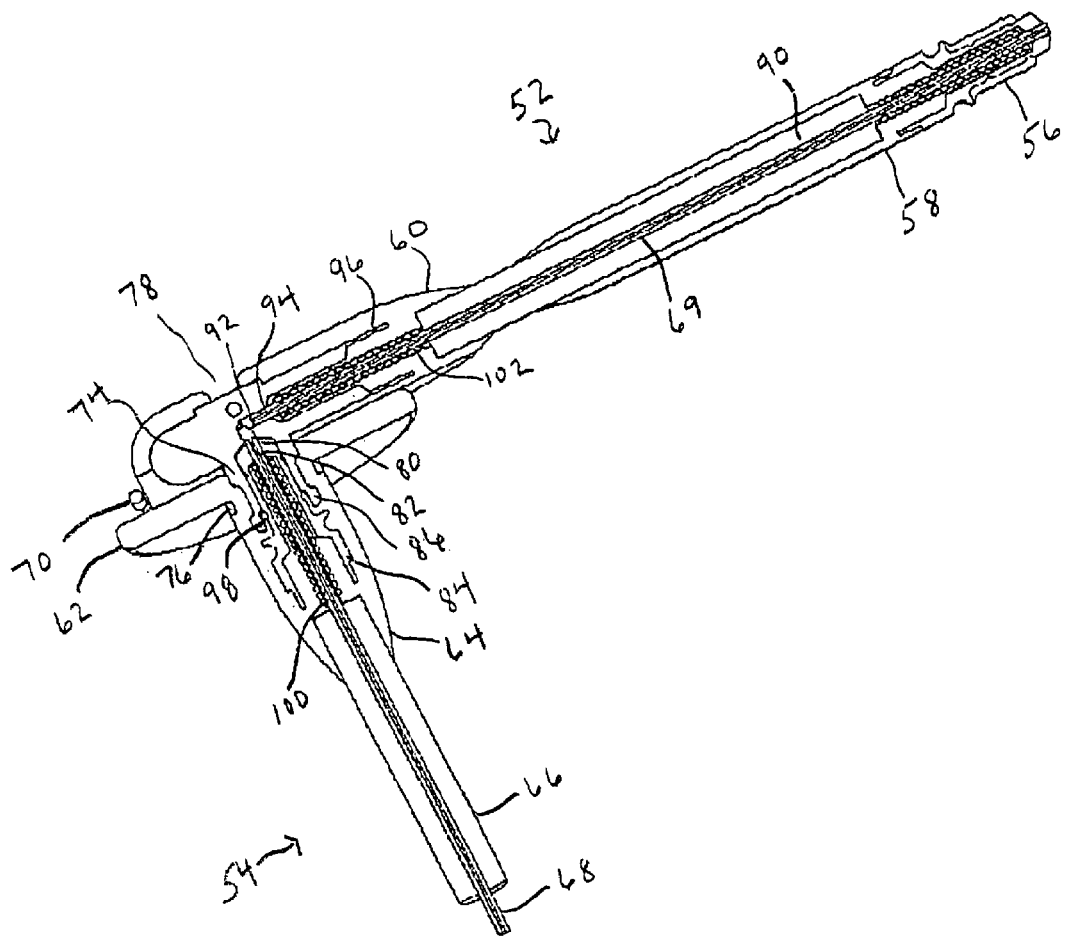
FIG. 10 shows a perspective, cutaway view of an interface between a first tubular member and a second tubular member of a modular catheter system according to an embodiment of the present invention.

FIG. 10 shows a perspective cutaway view of the interface between the first tubular member 52 and the second tubular member 54 when the first tubular member 52 and the second tubular member 54 are removably attached to one another. According to the embodiment of the invention shown in FIG. 10, as the first tubular member 52 and the second tubular member 54 engage each other, the extension recess 98, which may be thought of as a hollow interior portion of the extrusion 74, extends over the second seal molding 72 of the second tubular member 54. In addition, the extrusion 74 of the first tubular member 52 may extend into the second seal recess 86 of the second tubular member 54. According to an embodiment of the present invention, the extension recess 98 engages the second seal molding 72 and the extrusion 74 engages the second seal recess 86 by compression or friction fit. Other types of engagement schemes may also be used. For example, according to an embodiment of the present invention, a locking mechanism may be used to removably attach the first tubular member 52 to the second tubular member 54.

Thus, as can be seen in FIG. 10, a first seal may be formed between the first seal molding 84 and the second outer lumen 80 when the first tubular member 52 and the second tubular member 54 are removably attached to one another. The first seal molding 84 may encircle the second outer lumen 80 and the second inner lumen 82. In addition, a second seal may be formed when the second seal molding 72 engages the second header portion 64. Thus, the second seal may completely encircle the first seal and the second outer lumen 80 and the second inner lumen 82. Thus, according to the embodiment of the invention shown in FIG. 10, dual concentric seals surround and encircle the second outer lumen 80 and the second inner lumen 82, thereby ensuring that any fluids passing through the second catheter tubing 68 and the first catheter tubing 69 are confined to the interior portion of the modular catheter system 50. This allows the modular catheter system 50 to be fabricated with two parts, a first tubular member 52 and a second tubular member 54, that are removably attached to one another, without concern that fluids transported through the second catheter tubing 68 and the first catheter tubing 69 will leak into the area surrounding the catheter system 50, which is typically implanted into a human body.

It can also be seen in FIG. 10 that, when the first tubular member 52 and the second tubular member 54 are removably attached to one another, the first header portion of the first tubular member 52 may abut the disc 62 of the second tubular member 54, providing a stable interface between the first tubular member 52 and the second tubular member 54. In addition, the second header portion 64 may surround and completely encircle the second seal molding 72, providing yet another seal. Thus, in the embodiment of the invention shown in FIG. 10, three concentric seals have been formed. A first seal may be formed at the interface between the first seal molding 84 and the second outer lumen 80, a second seal may be formed between the second seal molding and the first seal molding 84, and a third seal may be formed between the second seal molding 72 and the second header portion 64, all of which are concentric. However, embodiments of the invention may be configured to have any number of concentric seals.

FIG. 11 shows a cutaway view of a compression fit interface between a first tubular member 52 and a second tubular member 54 when the first tubular member 52 and the second tubular member 54 are removably attached to one another according to an embodiment of the present invention. According to the embodiment of the invention shown in FIG. 11, as the first tubular member 52 and the second tubular member 54 engage each other, the extension recess 98, which may be thought of as a hollow interior portion of the extrusion 74, extends over the second seal molding 72 of the second tubular member 54. In addition, the extrusion 74 of the first tubular member 52 may extend into the second seal recess 86 of the second tubular member 54. According to the embodiment of the present invention shown in FIG. 11, the extension recess 98 engages the second seal molding 72 and the extrusion 74 engages the second seal recess 86 by compression. Thus, the first tubular member 52 and the second tubular member may connect to one another via compression fit.

FIG. 12 shows a perspective, cutaway view of the compression fit interface shown in FIG. 11. In FIG. 12, the second tubular member 54 is shown. The second seal molding 72 may be seen disposed adjacent the second seal recess 86.

The modular catheter system according to embodiments of the present invention has a variety of advantages over catheter systems of the prior art. In addition to reducing the risk of infection and minimizing trauma to the patient, portions of the modular catheter system that attach to implantable devices, such as the first tubular member, for example, that remain implanted for relatively long periods of time, may be fabricated with expensive components that will remain implanted. Inexpensive components may be placed in a removable portion of the modular catheter system, such as the second tubular member, for example. Thus, removing and replacing the removable portion of the modular catheter system becomes cost effective.

In addition, because embodiments of the invention may be fabricated using TEFLON or other fluoropolymers, which have a higher melting temperature than polyethylene, as an inner layer of the catheter tubing, the modular catheter system may be sterilized by autoclaving rather than EtO. As is well-known in the art, autoclaving is a less expensive method of sterilizing than EtO, which further adds to a reduced cost when preparing the catheter system for utilization.

Also, because embodiments of the present invention include, but are not limited to, a plurality of concentric seals, at least some of which are formed via a friction fit between at least two members, the pull force required to separate the friction-fitted joints may be at least 2.0 lbs. In addition, due to the integrity of the plurality of concentric seals, at least some of which are formed via a friction fit between at least two members, fluid may be passed through the catheter system at up to 200 psi and higher.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A modular catheter system comprising:
   a first tubular member comprising a first outer housing and a first header portion having a protrusion, the first tubular member having an axial dimension;
   a second tubular member comprising a second outer housing and a second header portion having a recess, the second tubular member having an axial dimension, the second tubular member configured to be movable relative to the first tubular member along the axial dimension of the second tubular member to removably attach the second tubular member to the first tubular member by receiving the protrusion of the first tubular member in the recess of the second tubular member;
   a first catheter tubing disposed within an interior portion of the first outer housing, the first catheter tubing defining a first linear fluid flow path extending along the axial dimension of the first tubular member; and
   a second catheter tubing disposed within an interior portion of the second outer housing, the second catheter tubing defining a second linear fluid flow path extending along the axial dimension of the second tubular member;
   wherein the second tubular member is configured such that a portion of the second catheter tubing extends along the axial dimension of the second tubular member into the first tubular member to position the second linear fluid flow path to be transverse to the first linear fluid flow path to form a continuous path when the second tabular member is removably attached to the first tubular member.

2. The modular catheter system according to claim 1, further comprising a plurality of concentric seals surrounding at least a portion of the first catheter tubing and the second catheter tubing.

3. The modular catheter system according to claim 2, wherein at least one of the plurality of concentric seals is formed when the second tubular member is removably attached to the first tubular member.

4. The modular catheter system according to claim 1, wherein, in a case where the second tubular member is removably attached to the first tubular member, the second tubular member and the first tubular member are disposed at an angle relative to each other, the angle being greater than 0 degrees and less than 180 degrees, and an end portion of the first catheter tubing defining the first linear fluid flow path and an end portion of the second catheter tubing defining the second linear fluid flow path are disposed relative to each other at an angle greater than 0 degrees and less than 180 degrees.

5. The modular catheter system according to claim 4, wherein, when the second tubular member is removably attached to the first tubular member, the angle at which the second tubular member and the first tubular member are disposed relative to each other is substantially a right angle.

6. The modular catheter system according to claim 1, further comprising
   a first coil surrounding at least a portion of the first catheter tubing; and
   a second coil surrounding at least a portion of the second catheter tubing,
   wherein the first coil maintains a position of first catheter tubing and the second coil maintains a position of second catheter tubing.

7. The modular catheter system according to claim 6, wherein the first coil and the second coil are springs.

8. The modular catheter system according to claim 3, further comprising:
   a third catheter tubing, the third catheter tubing disposed within an interior portion of the first tubular member and adjacent the first catheter tubing; and
   a fourth catheter tubing, the fourth catheter tubing disposed within an interior portion of the second tubular member and adjacent the second catheter tubing,
   wherein the third catheter tubing and the fourth catheter tubing form a continuous path in a case where the second tubular member is removably attached to the first tubular member.

9. The modular catheter system according to claim 8, wherein the first catheter tubing is concentric with the third catheter tubing and the second catheter tubing is concentric with the fourth catheter tubing.

10. The modular catheter system according to claim 8, wherein at least one of the plurality of concentric seals formed when the second tubular member is removably attached to the first tubular member encircles the third catheter tubing and the fourth catheter tubing.

11. The modular catheter system according to claim 1, wherein the protrusion of the first tubular member fits into the recess of the second tubular member via friction.

12. The modular catheter system according to claim 1, wherein the protrusion of the first tubular member fits into the recess of the second tubular member via compression.

13. The modular catheter system according to claim 1, wherein the first catheter tubing is a fluoropolymer.

14. The modular catheter system according to claim 2, wherein at least one of the plurality of concentric seals is titanium.

15. The modular catheter system according to claim 14, wherein the first catheter tubing is a fluoropolymer, and wherein the at least one titanium concentric seal abuts and encircles the fluoropolymer first catheter tubing.

16. The modular catheter system according to claim 15, wherein the first tubular member and the second tubular member are silicone.

17. The modular catheter system according to claim 16, wherein the silicone first tubular member and the silicone second tubular member abut and encircle at least one titanium concentric seal.

18. The modular catheter system according to claim 1, further comprising a coupling disposed at a distal end of the first tubular member,
   wherein the coupling is attachable to an implantable device, and
   wherein the second catheter tubing extends out of the second tubular member.

19. The modular catheter system according to claim 18, further comprising a sensor disposed within an interior portion of the second tubular member.

20. The modular catheter system according to claim 1, wherein:
   the first outer housing has an interior tubular wall that defines that outer periphery of the interior portion of the first outer housing;
   the first catheter tubing has an outer wall located within the outer periphery of the interior portion of the first outer housing;
   the second outer housing has an interior tubular wall that defines that outer periphery of the interior portion of the second outer housing; and
   the second catheter tubing has an outer wall located within the outer periphery of the interior portion of the second outer housing.

21. The modular catheter system according to claim 1, wherein the second catheter tubing extends along and beyond the entire length of the second tubular member and into the first tubular member when the second tubular member is removably attached to the first tubular member.

22. The modular catheter system according to claim 4, wherein, when the second tubular member is removably attached to the first tubular member, the protrusion of the first tubular member protrudes from the first header portion along the axial dimension of the second tubular member such that the first header portion and the second tubular member are disposed at the angle greater than 0 degrees and less than 180 degrees, relative to each other.

23. The modular catheter system according to claim 22, wherein, when the second tubular member is removably attached to the first tubular member, the angle at which the second tubular member and the first header portion are disposed relative to each other is substantially a right angle.

24. The modular catheter system according to claim 1, wherein the second catheter tubing extends along at least the entire length of the second tubular member and into the first tubular member when the second tubular member is removably attached to the first tubular member.

25. The modular catheter system according to claim 1,
   wherein, when the second tubular member is removably attached to the first tubular member, the protrusion protrudes from the first tubular member generally along the axial dimension of the second tubular member into the recess of the second tubular member.

26. The modular catheter system according to claim 4, wherein, when the second tubular member is removably attached to the first tubular member, the angle at which the end portion of the first catheter tubing and the end portion of the second catheter tubing are disposed relative to each other is a right angle.

27. The modular catheter system according to claim 1, wherein the first tubular member and the second tubular member contact each other such that the first linear fluid flow path and the second linear fluid flow path meet perpendicularly to form a continuous path when the second tubular member is removably attached to the first tubular member.

28. The modular catheter system according to claim 1, wherein the first catheter tubing is fixed relative to the first tubular member at all times during use of the modular catheter system.

29. The modular catheter system according to claim 1, wherein the first catheter tubing is not moveable relative to the first tubular member at all times during use of the modular catheter system.

30. The modular catheter system according to claim 1, wherein the first linear fluid flow path and the second linear fluid flow path meet each other in perpendicular directions in at least one of the first tubular member and the second tubular member when the second tubular member is removably attached to the first tubular member.

31. The modular catheter system according to claim 1, wherein the second tubular member is configured such that a portion of the second linear fluid flow path extends along the axial dimension of the second tubular member into the first tubular member to meet the first linear fluid flow path perpendicularly, when the second tubular member is removably attached to the first tubular member.

32. The modular catheter system according to claim 1, wherein the first linear fluid flow path and the second linear fluid flow path meet each other perpendicularly when the second tubular member is removably attached to the first tubular member.

* * * * *